United States Patent
Cadet et al.

[11] Patent Number: 5,877,407
[45] Date of Patent: Mar. 2, 1999

[54] PLASMA ETCH END POINT DETECTION PROCESS

[75] Inventors: Gardy Cadet, Orange, N.J.; Dale Edward Ibbotson, Windermere, Fla.; Tseng-Chung Lee, New York, N.Y.; Edward Alois Rietman, Madison, N.J.

[73] Assignee: Lucent Technologies Inc., Murray Hill, N.J.

[21] Appl. No.: 898,261

[22] Filed: Jul. 22, 1997

[51] Int. Cl.⁶ .................. G01H 5/00; G01N 29/02; H01L 21/3065
[52] U.S. Cl. .................. 73/24.01; 73/597; 216/59
[58] Field of Search .................. 73/24.01, 24.05, 73/24.06, 597; 216/59, 60

[56] References Cited

U.S. PATENT DOCUMENTS 5,392,635  2/1995  Cadet et al. .................. 73/24.01
5,501,098  3/1996  Cadet et al. .................. 73/24.01

*Primary Examiner*—John E. Chapman
*Attorney, Agent, or Firm*—Patricia A. Verlangieri

[57] ABSTRACT

A method for determining the endpoint of a plasma etch process is disclosed. The endpoint of the plasma etch process is determined using an acoustic cell attached to an exhaust port on a reaction chamber of a plasma reactor. At least a portion of the gas from the reaction chamber flows into the acoustic cell during the plasma etch process. Acoustic signals are periodically transmitted through the gas flowing in the acoustic cell and a first velocity for the acoustic signals associated with etching a first material layer formed on a substrate is determined. Thereafter, the endpoint of the plasma etch step is determined when the first velocity changes to a second velocity associated with etching the first material layer through its thickness to its interface with an underlying material layer. The gas from the reaction chamber optionally flows through a compressor prior to flowing into the acoustic cell. The compressor increases the pressure of the gas that flows into the acoustic cell.

12 Claims, 4 Drawing Sheets

PLASMA ETCH END POINT DETECTION PROCESS

1. FIELD OF THE INVENTION

The present invention relates generally to plasma systems and, more particularly, to a method for determining the endpoint of a plasma etch process.

2. DESCRIPTION OF THE RELATED ART

In many processes for device fabrication, a pattern defined by a lithographic technique is transferred through a layer of material formed on the surface of a substrate. Typically, the pattern is transferred by etching using a plasma. The term plasma, as used in this disclosure, refers to a partially ionized gas consisting of positively and negatively charged molecular species, as well as neutrals.

Plasma etching processes are typically performed in an apparatus such as a plasma reactor. Plasma reactors generally include a reaction chamber, a plasma generating system, a wafer holder and handling system and a gas delivery system (i.e. inlet, exhaust and flow control). The term reaction chamber, as used in this disclosure, refers to the area within a plasma reactor where ionized gases physically and/or chemically interact with a material layer formed on the surface of a substrate.

A cross-sectional view of an example of a plasma reactor, called a parallel plate reactor 10 is shown in FIG. 1. Parallel plate reactor 10 includes two electrodes 11, 12 positioned parallel to each other in a reaction chamber 14. Substrates 15 with lithographically defined patterns (not shown) formed thereon are placed on the surface 12a of electrode 12. In a typical etching process using a plasma reactor such as a parallel plate reactor 10, gases are mixed and introduced into the reaction chamber 14. The mixed gases flow between electrodes 11, 12. An electric field applied between electrodes 11, 12 ionizes the gases and forms a plasma 13. The plasma 13 then etches the layer of material (not shown) formed on the surface of substrates 15 and transfers the lithographically defined pattern therethrough.

A problem associated with plasma etching processes is a difficulty in determining when the etch step has been completed. This difficulty occurs because plasma techniques are typically timed processes, based on predetermined etch rates. The predetermined etch rates are identified by performing a calibration step. Since the exact conditions (i.e., pressure, gas flow, electric field) used during the calibration step are typically not duplicated for the etch step, timed processes are inaccurate and only provide an estimate as to when the plasma etch process is completed.

In order to avoid the use of timed processes for determining the endpoint of an etch step, diagnostic techniques have been developed which analyze the plasma in the reaction chamber. One such technique, called optical emission spectroscopy, monitors the intensity of the optical emission in the plasma. The intensity of the optical emission is related to the concentration of molecular species in the plasma. The completion of the etch process is determined when a change in the intensity of the optical emission is observed. A change in the intensity of the optical emission is observed when the concentration of molecular species in the plasma changes as a result of etching through the top layer and into the underlying substrate. Optical emission techniques require the reaction chamber to be equipped with an optical port for monitoring the optical emission of the plasma. Optical ports are not universally available in production environments, which limits the use of optical emission techniques for plasma etch endpoint detection.

Other diagnostic techniques such as laser interferometry, ellipsometry and mass spectrometry have been utilized in laboratory environments to identify the endpoint of an etch process. However, these techniques are both expensive and difficult to implement. In addition, optical ports are required to monitor the plasma etch process using laser interferometry and/or ellipsometry. While optical ports are not required to perform mass spectrometry, the detectors used for such techniques are placed in the reaction chamber and are often corroded by the etchants used for etching the material layers, limiting the ability of the detectors to accurately detect the completion of the etch step.

Accordingly, techniques useful for determining when an etch step is complete and which do not rely on the optical emissions of the plasma or direct optical access to the substrate in the reaction chamber and which are not corroded by the chemical gases used for such processes, are sought.

SUMMARY OF THE INVENTION

The present invention is directed to a method for determining the endpoint of a plasma etch process. For the purpose of this description, the endpoint of the plasma etch process refers to when a first material layer formed on the surface of a substrate is etched through its thickness to its interface with an underlying material layer.

The endpoint of the plasma etch process is determined using an acoustic cell. The acoustic cell is configured to have a transmitter and a receiver located at opposite ends of a conduit. The transmitter and the receiver are acoustically matched transducers, which preferably operate in the kilohertz range. Transducers suitable for use in acoustic cells are well known to those skilled in the art. One example of such a transducer is a lead-zirconate-titanate crystal.

In the process of the present invention, at least a portion of a gas stream from a reaction chamber of a plasma reactor flows through the acoustic cell, during the plasma etch process. The pressure at which the gas stream flows in the acoustic cell is preferably at least about 10 torr. Gas streams with pressures less than about 10 torr are undesirable because acoustic signals are not easily transmitted through gas streams at such pressures.

As the gas stream from the reaction chamber flows in the acoustic cell, acoustic signals are periodically transmitted from the transmitter to the receiver and the velocity of such acoustic signals is determined. The acoustic signals are periodically transmitted at intervals of at least about 20 hz (hertz), for the duration of the etch process. The acoustic signals, when transmitted, preferably travel a distance less than about 6 inches in the acoustic cell. The acoustic signals are transmitted at a frequency within the range of about 50 kilohertz to about 500 kilohertz.

The velocity of an acoustic signal is related to the average molecular weight of the gas stream according to the expression $$v_s = \sqrt{\frac{\gamma RT}{M}} \quad (1)$$

where $v_s$ is the velocity of the acoustic signals, R is the universal gas constant (8.3143 J/mol K), T is the temperature in degrees Kelvin, M is the average molecular weight of the gas, and $\gamma$ is the ratio of the average specific heat at constant pressure to the average specific heat at constant volume ($C_p/C_v$). Thus, at constant temperatures, the velocity of an acoustic signal changes as the average molecular weight of the gas changes. For example, if the average molecular weight of the gas decreases, the velocity of acoustic signals transmitted through the gas increases.

As the first material layer formed on the surface of a substrate is etched, the average molecular weight of the gas flowing in the acoustic cell does not vary significantly. Thus, from equation (1), the velocity of the acoustic signals transmitted through the gas exhausted from the reaction chamber as the first material layer is etched approximates a constant value. For the purpose of this description, the acoustic signals transmitted through the gas exhausted from the reaction chamber when the first material layer formed on the surface of the substrate is etched, have a first velocity (or reference velocity).

When the first material layer is etched through its thickness to its interface with the underlying material layer, the average molecular weight of the gas flowing into the acoustic cell changes. The change in the average molecular weight of the gas changes the speed at which the acoustic signals are transmitted through the gas in the acoustic cell. Thus, the first velocity determined for the acoustic signals transmitted through the gas as the first material layer is etched, changes to a second velocity associated with reaching the interface of the underlying material layer. The second velocity for the acoustic signals differs from the first velocity by more than 1%. The etch process endpoint occurs when the second velocity for the acoustic signals transmitted through the gas, is observed.

Since acoustic signals are not easily transmitted through gases at low pressures (less than about 10 torr), the ability to determine the endpoint of a low pressure plasma etch process is potentially limited. In an alternate embodiment of the present process, at least a portion of the gas stream from the reaction chamber flows through a compressor prior to flowing into the acoustic cell. The compressor compresses the gas stream thereby increasing the pressure of the gas flowing into the acoustic cell. The gas flowing from the compressor into the acoustic cell preferably has a pressure greater than about 10 torr. Increasing the pressure of the gas stream flowing in the acoustic cell, provides a mechanism for determining the endpoint of a low pressure plasma etch process. Compressors suitable for use in the present process are well known to those skilled in the art. One example of such a compressor is a vacuum pump.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION

Figure 1:
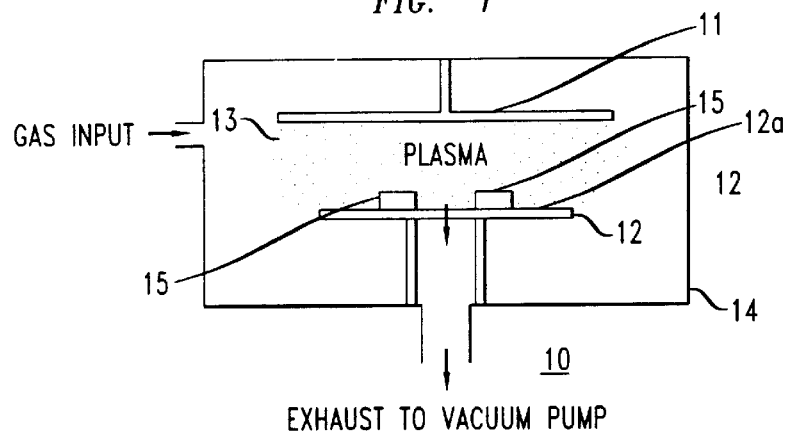
FIG. 1 shows a cross-sectional view of a parallel plate reactor.
Figure 2:
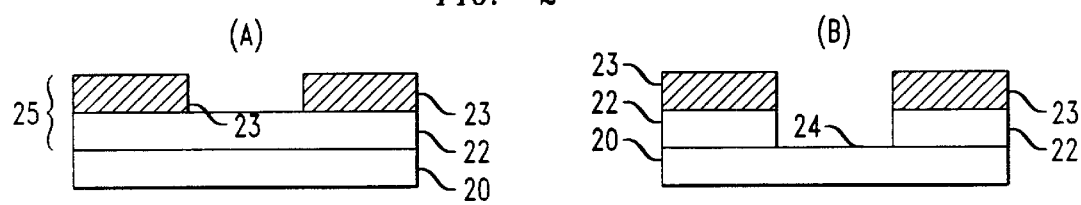
FIGS. 2A and 2B are illustrative of the process of the present invention wherein the endpoint of a plasma etch process is determined when a first material layer formed on the surface of a substrate is etched to the interface of an underlying material layer.

In the present process, the endpoint of a plasma etch step is determined. For the purpose of this description, the endpoint of the plasma etch step refers to when a first material layer formed on the surface of a substrate is etched through its thickness to its interface with an underlying material layer. For example, referring to FIG. 2A, there is shown a substrate 20 with a multilayered structure 25, thereon. Material layer 23 of the multilayered structure 25 is patterned; i.e, the layer is formed over a portion of the substrate. In a plasma etch process, the structure depicted in FIG. 2A is subjected to conditions that etch the exposed portion of layer 22. The endpoint of the etch process is reached when the exposed area of material layer 22 is etched through its thickness to its interface with substrate 20, as illustrated in FIG. 2B.

Figure 3:
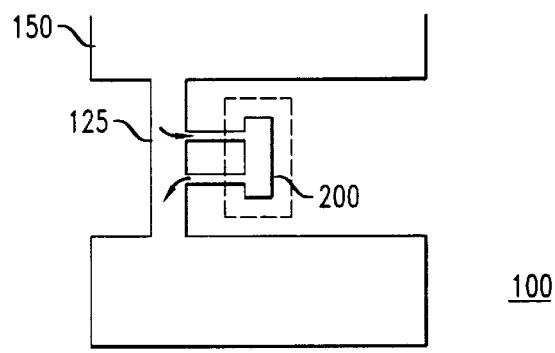
FIG. 3 is illustrative of the process of the present invention wherein an acoustic cell is attached to an exhaust port on a reaction chamber of a plasma reactor.

The endpoint of the plasma etch step is determined by monitoring the plasma during the etch step using an acoustic cell. The acoustic cell 200 (enclosed with dashed lines) is attached to an exhaust port 125 on a reaction chamber 150 of a plasma reactor 100, as shown in FIG. 3. Plasma reactors such as plasma reactor 100 are utilized in semiconductor device fabrication to generate a plasma in which material layers (e.g., silicon dioxide, polysilicon, and aluminium) formed on the surface of semiconductor substrates are etched.

Figure 4:
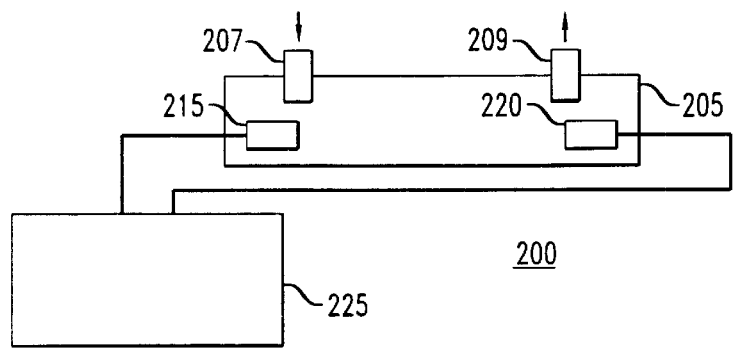
FIG. 4 is a cross-sectional view of an acoustic cell suitable for use in the process of the present invention.

Acoustic cell 200, shown in greater detail in FIG. 4, is configured to have a transmitter 215 and a receiver 220 located at opposite ends of a conduit 205. The transmitter 215 and the receiver 220 are acoustically matched transducers. Transducers suitable for use in acoustic cells are well known to those skilled in the art. One example of a suitable transducer is a lead-zirconate-titanate crystal.

Conduit 205 has two gas ports 207 and 209. Gas port 207 is located near a first end of the conduit 205 and gas port 209 is located near a second end of the conduit 205, opposite the first end. Gas ports 207 and 209 are configured to allow a gas stream to flow through the conduit 205. Conduit 205 is formed from a material that is not substantially degraded or affected by the exhaust gas from the plasma reactor. For example, type 316 stainless steel is not significantly degraded by carbon tetrafluoride ($CF_4$) gas, which is typically used to etch silicon dioxide.

Transmitter 215 and receiver 220 are connected to a signal generator/processor 225. Signal generator/processor 225 instructs transmitter 215 to transmit acoustic signals and then records these same signals when they are detected by receiver 220. The acoustic signals that are transmitted in acoustic cell 200 preferably travel a distance less than about 6 inches from the transmitter 215 to the detector 220. Acoustic signals which travel distances greater than about 6 inches are undesirable because such acoustic signals are not easily detected, when transmitted according to the conditions described herein.

Acoustic cells such as acoustic cell 200, briefly discussed above, are well known to those skilled in the art. Examples of acoustic cells suitable for use in the process of the present invention are described in U.S. Pat. No. 5,392,635 and U.S. Pat. No. 5,501,098, hereby incorporated by reference.

In the process of the present invention, at least a portion of the gas stream exhausted from the reaction chamber 150 of the plasma reactor 100 flows through the acoustic cell 200. The gas stream flows through the acoustic cell during the plasma etch step. The pressure at which the gas stream flows in the acoustic cell is preferably greater than about 10 torr. Pressures less than about 10 torr are undesirable because acoustic signals are not easily transmitted through low pressure gas streams.

As the gas stream from the reaction chamber 150 flows in the acoustic cell 200, acoustic signals are periodically transmitted from the transmitter 215 to the receiver 220, and the velocity of such acoustic signals is determined by the signal generator/processor 225. The acoustic signals are periodically transmitted at intervals of at least about 20 hertz, for the duration of the plasma etch step. The acoustic signals are transmitted at a frequency within the range of about 50 kilohertz to about 500 kilohertz.

Signal generator/processor 225 utilizes a measurement technique such as, for example, time-of-flight, to determine the velocity of each acoustic signal transmitted from the transmitter 215 to the receiver 220. For example, the distance between transmitter 215 and receiver 220 defines a fixed distance in conduit 205. Thus, signal generator/processor 225 determines the speed of the transmitted acoustic signal by measuring the time required for such acoustic signal to travel along the conduit 205 from the transmitter 215 to the receiver 220. Signal generator/processor 225 optionally determines the velocity of each acoustic signal by monitoring the frequency of the transmitted acoustic signals, as described below.

When acoustic signals are propagated through gases, such acoustic signals generate a disturbance that imparts directional energy to nearby molecules in the gas, creating energized gas molecules in the vicinity of the disturbance. Thereafter, via collisions between gas molecules, the energized gas molecules impart directional energy to contiguous gas molecules. Such collisions between contiguous gas molecules describes the mechanism for propagating acoustic signals through the gas.

Since the propagation of the acoustic signals is a function of the collisions between contiguous gas molecules, the velocity of the acoustic signals that are propagated through the gas is dependent upon the mean free path, $\lambda$, of the gas molecules. The mean free path, $\lambda$, refers to the average distance traveled by a gas molecule between collisions with other gas molecules, and is determined from $$\lambda = \frac{1}{P\sqrt{2}\ \pi N d^2} \quad (2)$$

where P is the pressure, N is the number density of gas molecules, and d is the effective diameter of the gas molecules in meters.

Also, the velocity, $v_s$, of the acoustic signals is of the same order of magnitude as the mean translational speed, c, of the energized gas molecules, $$v_s \approx \bar{c} \quad (3)$$

since such acoustic signal transmission is a function of molecular collisions.

The mean translational speed of the energized gas molecules, c, is calculated from $$\bar{c} = \sqrt{\gamma \frac{P}{\rho}} \quad (4)$$

where P is the pressure, $\gamma$ is the ratio of the specific heat at constant pressure to the specific heat at constant volume $(C_p/C_v)$, and $\rho$ is the density. The pressure, P, can also be determined from $$P = \frac{NRT}{V} \quad (5)$$

and the density, $\rho$, from $$\rho = \frac{NM}{V} \quad (6)$$

Figure 5:
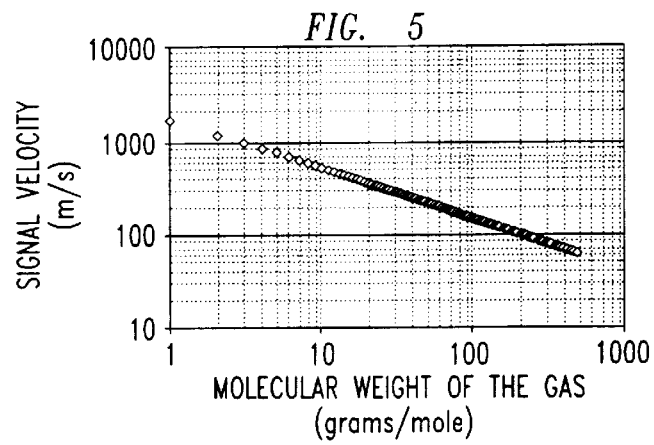
FIG. 5 is a plot illustrating the relationship of the molecular weight of a gas to the signal velocity of acoustic signals.

For equations (5) and (6), N is the number density of gas molecules, R is the universal gas constant (8.3143 J/mol K), T is the absolute temperature in degrees Kelvin, V is the volume, and M is the molecular weight of the gas. Substituting equations (5) and (6) into equation (4) provides, $$v_s = \sqrt{\frac{\gamma RT}{M}} \quad (7)$$

which expresses the relationship between the velocity, $v_s$, of the transmitted acoustic signals and the molecular weight, M, of the gas. At constant temperatures, equation (7), depicted graphically in FIG. 5, illustrates that the velocity, $v_s$, of the transmitted acoustic signals changes as the average molecular weight, M, of the gas is varied. Specifically, the velocity of the transmitted acoustic signals decreases as the average molecular weight of the gas increases.

Equation (7), which illustrates the relationship between the velocity of the transmitted acoustic signals and the average molecular weight of the gas, is applicable to the endpoint detection process of the present invention. When the first material layer formed on the surface of the substrate is etched, the average molecular weight of the gas stream does not vary significantly. The average molecular weight of the gas stream does not vary significantly because the composition of the gas stream remains substantially unchanged during the etch step. Thus, from equation (7), the velocity of the acoustic signals transmitted through the gas stream as the first material layer is etched approximates a constant value. For the purpose of this description, the velocity of the acoustic signals transmitted through the gas stream when the first material layer is etched have a first velocity (or a reference velocity).

When the first material layer is etched through its thickness to its interface with the underlying material layer, as shown in FIG. 2B, the average molecular weight of the gas flowing into the acoustic cell changes. The average molecular weight of the gas flowing in the acoustic cell changes because the composition of the gas changes when the interface of the underlying material layer is reached.

The change in the average molecular weight of the gas stream affects the velocity of the acoustic signals transmitted through the gas in the acoustic cell. Thus, the first velocity determined for acoustic signals transmitted through the gas as the first material layer is etched changes to a second velocity. The second velocity, which is different from the first velocity by more than 1%, is associated with reaching the interface of the underlying material layer. The endpoint of the plasma etch step occurs when the second velocity is determined.

The endpoint detection process of the present invention is sensitive to small changes in the molecular weight of the gas stream. For example, at room temperature (25° C.), equation (7) reduces to $$v_s = \frac{56.94}{\sqrt{M}} \quad (8)$$

Figure 6:
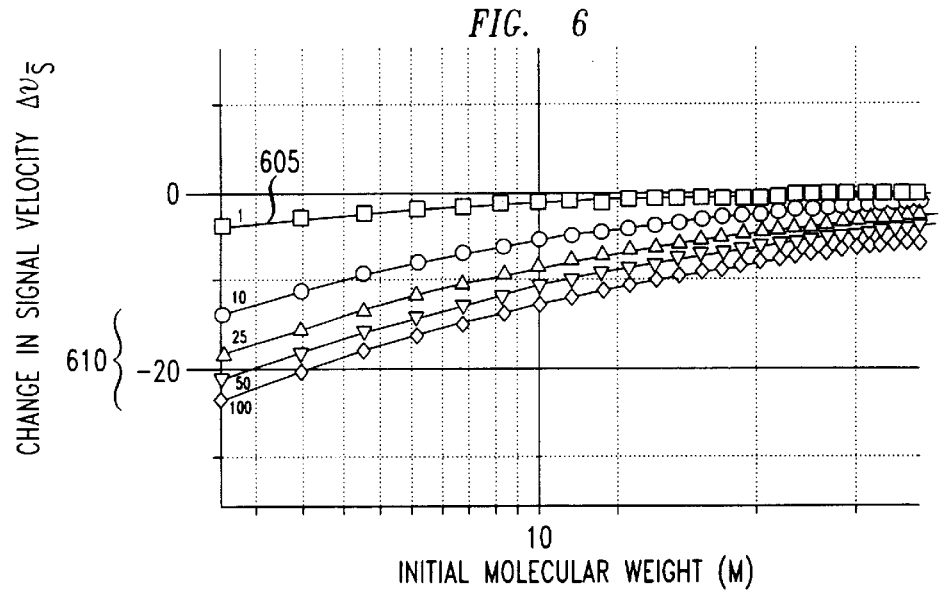
FIG. 6 is a plot of the change in the signal velocity ($\Delta v_s$) of acoustic signals as a function of the initial molecular weight (M) of the gas.

Thus, from equation (8), a change in the signal velocity, $\Delta v_s$, is expressed as $$\Delta v_s = \frac{56.94}{\sqrt{M + \Delta M}} - v_s \quad (9)$$

where $v_s$ is the first velocity for acoustic signals transmitted through the gas as the first material layer is etched, M is the molecular weight of the gas during the plasma etch step, and $\Delta M$ is the change in molecular weight of the gas when the interface of the underlying material layer is reached. Equation (9), graphically illustrated in FIG. 6, describes changes to the velocity of an acoustic signal as a function of changes in the molecular weight of the gas. Each curve on this graph is plotted for a different $\Delta M$ (i.e., 1 gram/mole, 10 grams/mole, 25 grams/mole, 50 grams/mole and 100 grams/mole). For example, if the molecular weight of the gas during the plasma etch step is initially about 10 grams/mole, thereafter a small change in the molecular weight (about 1 gram/mole) of the gas, corresponds to a change in the velocity for the acoustic signals of about 1–2 m/s (meters/second), as determined using the line denoted as 605. If the change in molecular weight of the gas is larger (about 10–50 grams/mole), the change in the velocity of the acoustic signal is also increased (about 12–20 m/s), as determined using the line denoted as 610.

An example of an alternative embodiment for measuring small changes (about 1–10 grams/mole) in the molecular weight of the gas in the acoustic cell, monitors the frequency of the acoustic signals transmitted through the gas. When the mean free path between constituents in the gas is about 1 cm, the signal velocity ($v_s$) is related to the frequency (f) of the acoustic signals by the equation $$v_s = 10^{-2} f. \quad (10)$$

Figure 7:
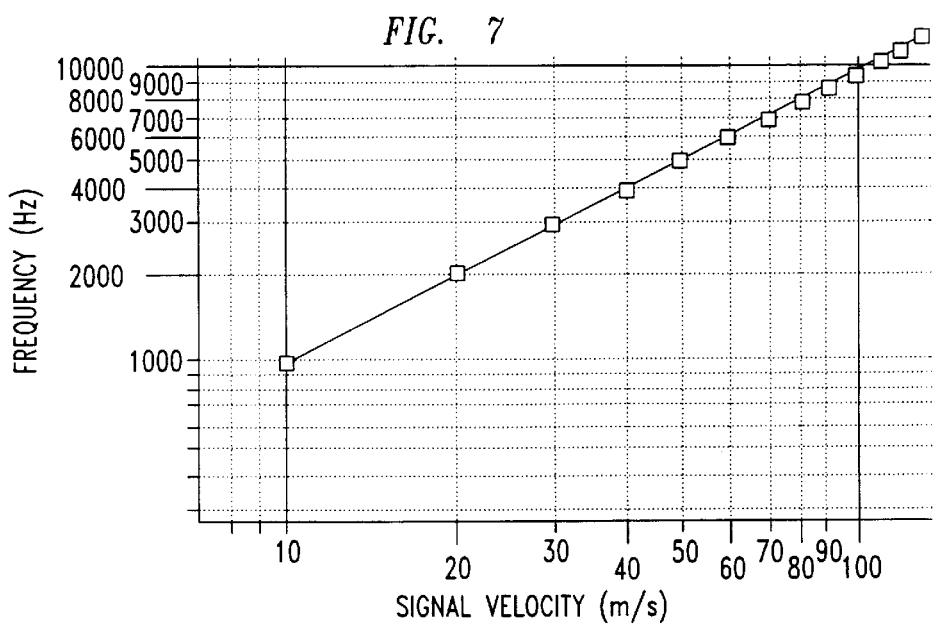
FIG. 7 is a plot illustrating the relationship of the signal velocity of acoustic signals to the frequency.

Equation (10) is graphically illustrated in FIG. 7, which shows that for a small change in the velocity of an acoustic signal, the corresponding frequency change of the acoustic signal is two orders of magnitude larger. For example, referring to FIG. 7, if the velocity of an acoustic signal changes by about 10 m/s, there is a corresponding increase in the frequency of such acoustic signal of about 1000 hertz. Thus, the 1 gram/mole change in the molecular weight of the gas, which causes a change of about 1–2 m/s in the velocity, causes a change of about 100–200 hertz in the frequency of the transmitted acoustic signals.

At low pressures (less than 10 torr), the molecular density of gas molecules in the gas is reduced, increasing the mean free path, $\lambda$, of the gas molecules. The increase in the mean free path of the gas molecule results in fewer collisions between gas molecules, inhibiting the mechanism for transmitting acoustic signals in the gas, as discussed above.

Figure 8:
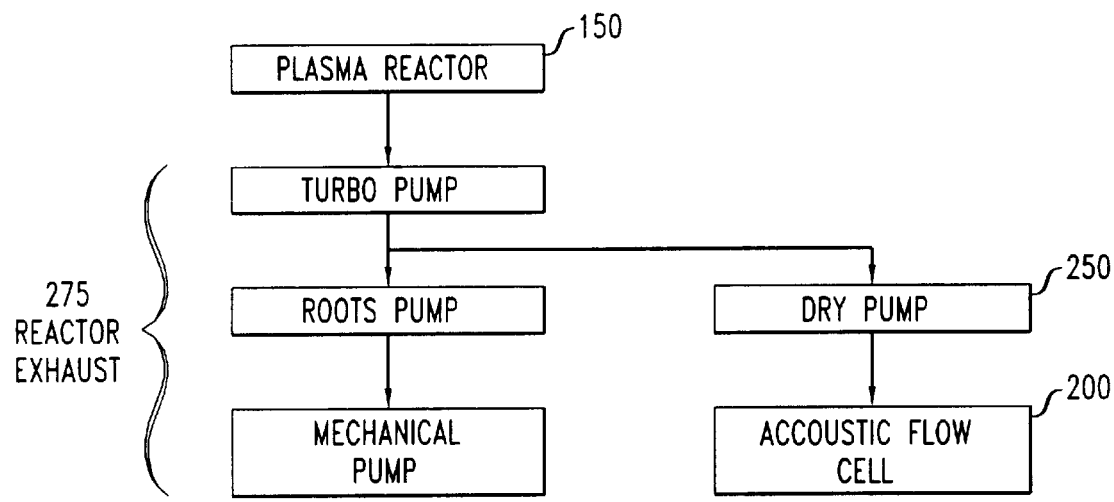
FIG. 8 is illustrative of the process of the present invention wherein a compressor compresses the gas exhausted from the reaction chamber of the plasma reactor thereby increasing the pressure of the gas which flows into the acoustic cell.

Since the efficiency of acoustic signal propagation decreases with decreasing pressure, the ability to determine the endpoint of a low pressure plasma etch step is potentially affected. In an alternate embodiment of the present process, at least a portion of the gas from the reaction chamber 150 flows through a compressor 250 prior to flowing into acoustic cell 200, as shown in FIG. 8. Compressor 250 compresses the gas stream thereby increasing the pressure of the gas flowing into acoustic cell 200. The pressure of the gas flowing into acoustic cell 200 from compressor 250 is preferably greater than about 10 torr. Compressors suitable for use in the present process are well known to those skilled in the art. One example of such a compressor is a Dryvac Model 25P vacuum pump available from Leybold Vacuum Products, Export, Pa.

The following examples are illustrative of conditions employed for transmitting acoustic signals in acoustic cells which are filled with gases at various pressures.

EXAMPLE 1

An acoustic cell made of 316 stainless steel was filled with air which had a temperature of about 25° C. The air in the acoustic cell was kept at a pressure of about 44 torr. The acoustic cell was an AT&T model GC-113, manufactured by Massa Products, Hangham, Mass.

Acoustic signals which had a frequency of about 200 kilohertz were transmitted through the air in the acoustic cell from the transmitter to the detector with a repetition rate of about 100 hz. The acoustic signals traveled a distance of about 6 inches from the transmitter to the detector.

Figure 9:
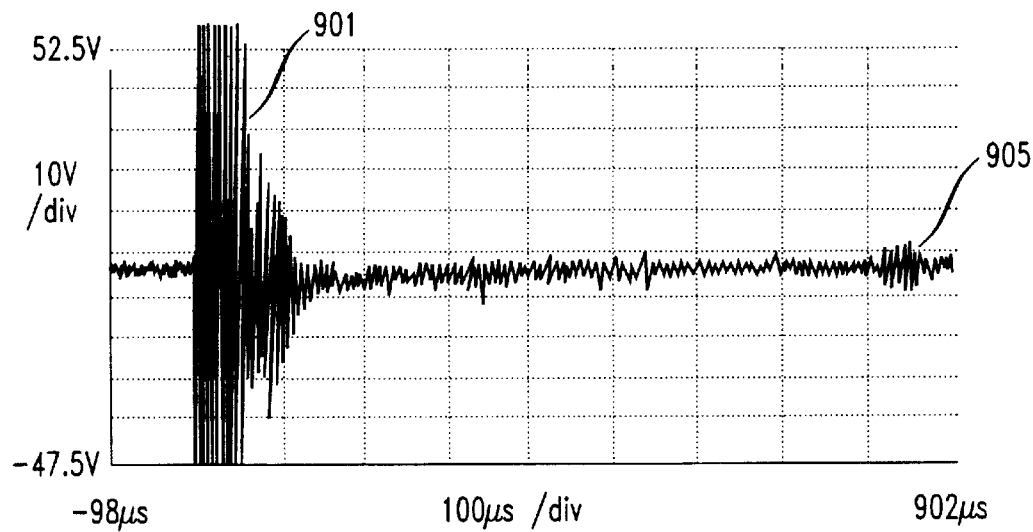
FIG. 9 is an illustration of a signal analyzer trace for the acoustic signals described in Example 1.

A DSA Model 602 digitizing signal analyzer (available from Tektronix, Inc.) was used to monitor the acoustic signals transmitted through the air in the acoustic cell. A trace from the digitizing signal analyzer is illustrated in FIG. 9. The pulse, denoted as 901, is the transmitted acoustic signal. The pulse, denoted as 905, is the detected acoustic signal. FIG. 9 illustrates the capability of transmitting acoustic signals through air at pressures of about 44 Torr.

EXAMPLE 2

The acoustic cell described in Example 1 was filled with air that had a temperature of about 25° C. The air in the acoustic cell was kept at a pressure of about 20 Torr. Acoustic signals were transmitted a distance of about 3 inches from the transmitter to the detector, according to the same conditions described in Example 1.

Figure 10:
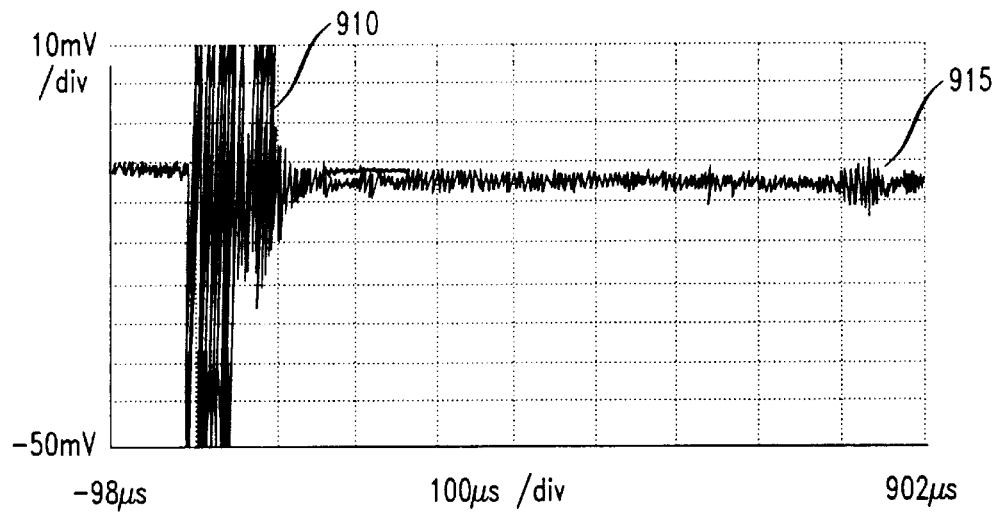
FIG. 10 is an illustration of a signal analyzer trace for the acoustic signals described in Example 2.

A DSA Model 602 digitizing signal analyzer was used to monitor the acoustic signals transmitted through the air in the acoustic cell. A trace from the digitizing signal analyzer is illustrated in FIG. 10. The pulse, denoted as 910, is the transmitted acoustic signal. The pulse, denoted as 915, is the detected acoustic signal. FIG. 10 illustrates the capability of transmitting acoustic signals through air at pressures of about 20 Torr.

EXAMPLE 3

The acoustic cell described in Example 1 was filled with tetraethyl orthosilicate (TEOS) gas in oxygen that had a temperature of about 32° C. The TEOS gas in the acoustic cell was kept at a pressure of about 12 Torr.

Acoustic signals which had a frequency of about 200 kilohertz were transmitted through the TEOS gas in the acoustic cell from the transmitter to the detector with a repetition rate of about 100 hz. The acoustic signals traveled a distance of about 3 inches from the transmitter and the detector.

Figure 11:
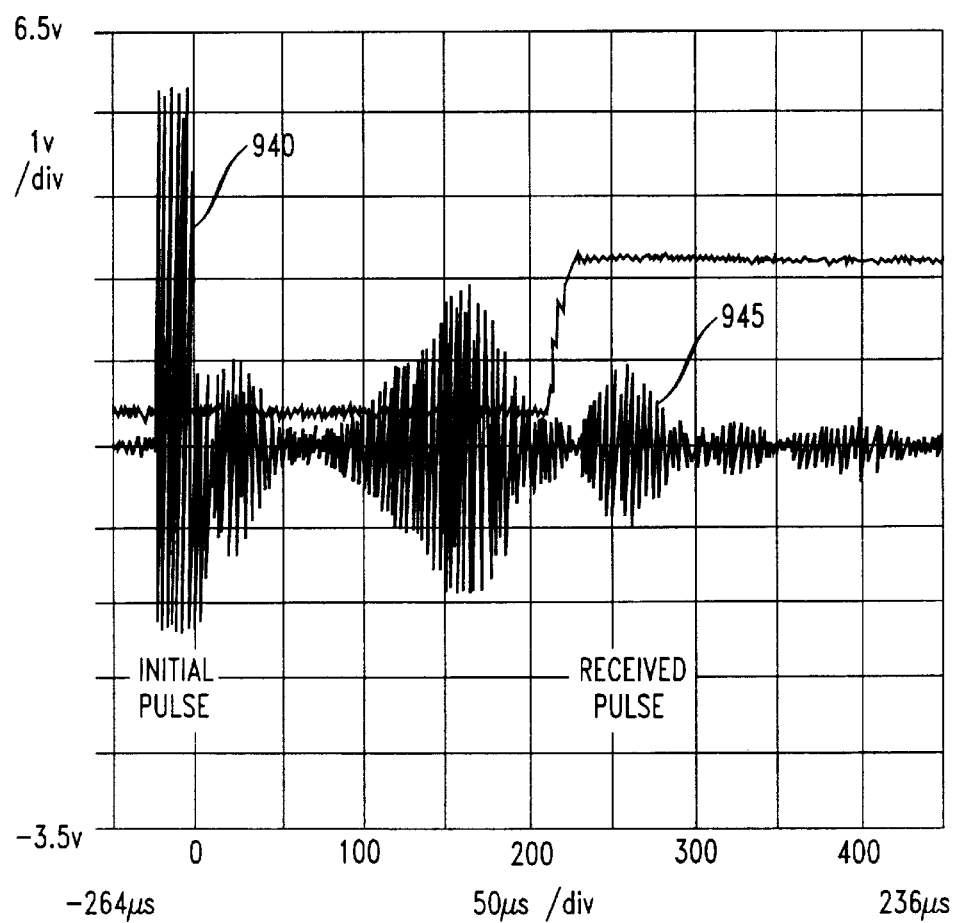
FIG. 11 is an illustration of a signal analyzer trace for the acoustic signals described in Example 3.

A DSA Model 602 digitizing signal analyzer was used to monitor the acoustic signals transmitted through the TEOS gas in the acoustic cell. A trace from the digitizing signal analyzer is illustrated in FIG. 11. The pulse, denoted as 940, is the transmitted acoustic signal. The pulse, denoted as 945, is the detected acoustic signal. Additional pulses shown on the trace which surround those denoted as 940 and 945 are attributed to noise from the acoustic cell. FIG. 11 illustrates the capability of transmitting acoustic signals through TEOS gas at pressures of about 12 Torr.

The invention claimed is:

1. A method for determining an endpoint of a plasma etch process, comprising the steps of:

introducing reactant gases into a reaction chamber of a plasma generator and generating a plasma;

subjecting a substrate with at least a first material layer formed thereon to the plasma, whereby the first material layer is etched by the plasma;

introducing at least a portion of a gas stream from the reaction chamber into an acoustic cell during the plasma etch process;

transmitting an acoustic signal through the gas stream in the acoustic cell;

monitoring the acoustic signal transmitted through the gas stream during the plasma etch process; and determining the endpoint of the plasma etch process in response to an observed change in the monitored acoustic signal.

2. The method of claim 1 further comprising determining a signal velocity for the acoustic signal transmitted through the gas stream in the acoustic cell, wherein the signal velocity is a function of the molecular weight of the gas stream.

3. The method of claim 2, wherein the signal velocity of the acoustic signal is monitored during the plasma etch process and a change in the signal velocity of the acoustic signal is associated with a change in the molecular weight of the gas stream, indicative of the endpoint of the plasma etch process.

4. The method of claim 1, wherein the acoustic signal transmitted through the gas stream in the acoustic cell has a frequency which is a function of the molecular weight of the gas stream.

5. The method of claim 4, wherein the frequency of the acoustic signal is monitored during the plasma etch process and a change in the frequency of the acoustic signal is associated with a change in the molecular weight of the gas stream, indicative of the endpoint of the plasma etch process.

6. The method of claim 1, wherein the gas stream introduced into the acoustic cell during the plasma etch process has a pressure greater than about 10 torr.

7. The method of claim 1 further comprising the step of compressing the gas stream from the reaction chamber of the plasma reactor prior to introducing such gas stream into the acoustic cell.

8. The method of claim 1, wherein the acoustic signal is transmitted a distance less than about 6 inches in the acoustic cell.

9. The method of claim 1, wherein the acoustic signal is transmitted at intervals of at least about 20 hertz.

10. The method of claim 1, wherein the acoustic signal is transmitted at a frequency within the range of about 50 kilohertz to about 500 kilohertz.

11. The method of claim 2, wherein the signal velocity is determined by monitoring the frequency of the transmitted acoustic signal.

12. The method of claim 7, wherein the gas stream from the reaction chamber is compressed using a vacuum pump.

\* \* \* \* \*